(12) United States Patent
McIntosh et al.

(10) Patent No.: US 7,883,501 B2
(45) Date of Patent: Feb. 8, 2011

(54) MULTIPLE RATIO FLUID DISPENSER

(75) Inventors: Kevin D. McIntosh, Brooklyn Park, MN (US); Richard M. Albrecht, Maple Grove, MN (US)

(73) Assignee: Arteriocyte Medical Systems, Inc., Cleveland, OH (US)

( * ) Notice: Subject to any disclaimer, the term of this patent is extended or adjusted under 35 U.S.C. 154(b) by 0 days.

(21) Appl. No.: 12/462,885

(22) Filed: Aug. 10, 2009

(65) Prior Publication Data

US 2009/0306623 A1 Dec. 10, 2009

Related U.S. Application Data

(60) Division of application No. 10/876,147, filed on Jun. 24, 2004, now Pat. No. 7,604,626, which is a continuation of application No. 10/212,430, filed on Aug. 5, 2002, now Pat. No. 6,936,033.

(60) Provisional application No. 60/388,822, filed on Jun. 14, 2002.

(51) Int. Cl.
*A61M 31/00* (2006.01)
(52) U.S. Cl. ...................................... 604/506
(58) Field of Classification Search ............. 604/82–86, 604/181–182, 187, 191, 506–511, 500, 4.01–6.16; 222/145.5, 145.6, 137, 386
See application file for complete search history.

(56) References Cited

U.S. PATENT DOCUMENTS

| | | | |
|---|---|---|---|
| 2,112,160 A | 3/1938 | Johnson | 128/234 |
| 3,223,083 A | 12/1965 | Cobey | 128/92 |
| 3,467,096 A | 9/1969 | Horn | 128/218 |
| 4,040,420 A | 8/1977 | Speer | 128/218 |
| 4,109,653 A | 8/1978 | Kozam et al. | 128/218 |
| 4,359,049 A | 11/1982 | Redl et al. | 128/218 |
| 4,609,371 A | 9/1986 | Pizzino | 604/191 |
| 4,631,055 A | 12/1986 | Redl et al. | 604/82 |

(Continued)

FOREIGN PATENT DOCUMENTS

FR 2 722 104 1/1996

(Continued)

OTHER PUBLICATIONS

International Search Report for Application No. PCT/US03/18591 dated Sep. 30, 2003.

*Primary Examiner*—Manuel A Mendez
(74) *Attorney, Agent, or Firm*—Mintz Levin Cohn Ferris Glovsky and Popeo PC (57) ABSTRACT

A double syringe delivery system is disclosed for holding a pair of syringes in a manner so as to accommodate the simultaneous activation of the plunger of each syringe in order to effect simultaneous delivery of the contents of each syringe. The delivery system includes a delivery mechanism for delivering the contents of both syringes to a site of application. The delivery system further includes a support member that is positioned between the two syringe bodies. The elongated support member has resilient, C-shaped clamps on one end of the support member. The clamps are designed to be removably clamped onto the applicator so that the syringe barrels will be held together in a parallel manner. The elongated support member further comprises finger grips. A plunger connects the two syringe plungers so that they can also be simultaneously activated.

17 Claims, 6 Drawing Sheets

U.S. PATENT DOCUMENTS

| | | | |
|---|---|---|---|
| 4,735,616 A | 4/1988 | Eibl et al. | 604/191 |
| 4,874,368 A | 10/1989 | Miller et al. | 604/82 |
| 4,978,336 A | 12/1990 | Capozzi et al. | 604/82 |
| 4,979,942 A | 12/1990 | Wolf et al. | 604/83 |
| 5,104,375 A | 4/1992 | Wolf et al. | 604/56 |
| 5,116,315 A | 5/1992 | Capozzi et al. | 604/82 |
| 5,185,001 A | 2/1993 | Galanakis | 604/5 |
| 5,290,259 A | 3/1994 | Fischer | 604/218 |
| 5,322,510 A | 6/1994 | Lindner et al. | 604/82 |
| 5,368,563 A | 11/1994 | Lonneman et al. | 604/82 |
| 5,376,079 A | 12/1994 | Holm et al. | 604/191 |
| 5,445,614 A | 8/1995 | Haber et al. | 604/89 |
| 5,464,396 A | 11/1995 | Barta et al. | 604/191 |
| 5,474,540 A | 12/1995 | Miller et al. | 604/191 |
| 5,520,658 A | 5/1996 | Holm | 604/191 |
| 5,542,934 A | 8/1996 | Silver | 604/191 |
| 5,582,596 A | 12/1996 | Fukunaga et al. | 604/191 |
| 5,584,815 A | 12/1996 | Pawelka et al. | 604/191 |
| 5,605,255 A | 2/1997 | Reidel et al. | 222/137 |
| 5,643,206 A | 7/1997 | Fischer | 604/82 |
| 5,665,067 A | 9/1997 | Linder et al. | 604/82 |
| 5,725,499 A | 3/1998 | Silverstein et al. | 604/82 |
| 5,814,022 A | 9/1998 | Antanavich et al. | 604/191 |
| 5,851,169 A | 12/1998 | Meresz et al. | 494/12 |
| 5,887,755 A | 3/1999 | Hood, III | 222/135 |
| 5,975,367 A | 11/1999 | Coelho et al. | 222/137 |
| 5,989,215 A | 11/1999 | Delmotte et al. | 604/82 |
| 6,001,259 A | 12/1999 | Whitmore | 210/651 |
| 6,113,571 A | 9/2000 | Zinger et al. | 604/82 |
| 6,132,396 A | 10/2000 | Antanavich et al. | 604/82 |
| 6,234,994 B1 | 5/2001 | Zinger | 604/82 |
| 6,394,982 B1 | 5/2002 | Ehrenfels | 604/191 |
| 6,444,228 B1 | 9/2002 | Baugh et al. | 424/530 |
| 6,454,739 B1 | 9/2002 | Chang | 604/82 |
| 6,475,175 B1 | 11/2002 | Rivera et al. | 604/6.02 |
| 6,589,153 B2 | 7/2003 | Dolecek et al. | 494/18 |
| 6,596,180 B2 | 7/2003 | Baugh et al. | 210/782 |
| 6,612,975 B2 | 9/2003 | Malcom et al. | 494/84 |
| 6,719,901 B2 | 4/2004 | Dolecek et al. | 210/380.1 |
| 6,793,828 B2 | 9/2004 | Dolecek et al. | 210/787 |
| 6,936,033 B2 | 8/2005 | McIntosh et al. | 604/191 |
| 7,604,626 B2 * | 10/2009 | McIntosh et al. | 604/506 |
| 2002/0004038 A1 | 1/2002 | Baugh et al. | 424/93.7 |
| 2003/0232712 A1 | 12/2003 | Dolecek et al. | 494/37 |
| 2004/0055937 A1 | 3/2004 | Dolecek | 210/85 |

FOREIGN PATENT DOCUMENTS

| | | |
|---|---|---|
| WO | WO 95/31137 | 11/1995 |
| WO | WO 00/16698 | 3/2000 |

* cited by examiner

MULTIPLE RATIO FLUID DISPENSER

CROSS-REFERENCE TO RELATED APPLICATIONS

The present application is a divisional of U.S. patent application Ser. No. 10/876,147 filed on Jun. 24, 2004, now U.S. Pat. No. 7,604,626, issued on Oct. 20, 2009, which is a continuation of U.S. patent application Ser. No. 10/212,430 filed on Aug. 5, 2002, now U.S. Pat. No. 6,936,033, issued on Aug. 30, 2005, which claims priority to U.S. Provisional Patent Application Ser. No. 60/388,822, filed on Jun. 14, 2002. The disclosures of these applications are specifically incorporated herein by reference in their entireties.

BACKGROUND OF THE INVENTION

1. Field of the Invention

The invention is in the field of systems utilized to measure out and mix two or more fluids, including freely flowing fluids and viscous fluids, by delivering them simultaneously to a single location. More particularly, the invention's field concerns systems for simultaneously dispensing two nonhomogeneous materials from two syringes.

2. Description of the Prior Art

There are many types of procedures that require the mixing of two or more substances before the mixed compound can be used. For example, in the field of dentistry a common practice in the dental arts is to measure separate substances, drop-wise, into a well or mixing dish and to then mix the separate substances together using an applicator brush, which in turn is then used to apply the mixed compound to teeth surfaces. More recently, more advanced mixing and delivery applicator syringes have been devised that permit mixing to occur within the same syringe used for delivery. As will be appreciated, in dentistry, it is often necessary to mix relatively small amounts because of the small surface areas that are to be worked upon. Furthermore, the materials which are mixed are often expensive, and rather than mix large quantities, relatively small quantities are mixed repeatedly so as to not waste undue amounts of the materials in question.

There are circumstances in which it is desirable to dispense liquid or semi-liquid materials in a predetermined ratio. The materials may include reactive, two component adhesives, sealants, coating, or potting compounds, in which one material may comprise a resin compound and the other material a catalyst.

Clotting of blood in vivo takes place by conversion of the soluble plasma protein fibrinogen into fibrin, which spontaneously polymerizes into an insoluble gel matrix which may attach to adjacent tissue. The gel matrix stops bleeding and stabilizes structures. Thrombin catalyzed conversion of fibrinogen to fibrin can be reproduced in vitro and has great utility for adhering tissues and achieving hemostasis. Such fibrin sealants and fibrin glues are available commercially and are also made in blood processing laboratories.

Preparation and Use of Fibrinogen-Based Sealants Have Been Extensively Reviewed.

Fibrin sealants, fibrin glues and adhesives based on combining fibrinogen-containing solutions with thrombin-containing solutions are used to reduce bleeding and restore hemostasis during surgical procedures. They have been known and in use for many years during which technology has evolved significantly. For example, fibrin clots can be made using different concentrations of fibrinogen in conjunction with the thrombin solution. Subsequent developments in technology include cryoprecipitate fibrinogen. Concentrated plasma can be used as the fibrinogen component in fibrin sealants.

Similarly, various types of applicators for fibrin glue are known. An optimal design is not obvious because of the chemical and biological properties of the liquid resulting from combining fibrinogen and thrombin solutions. Because of the rapid polymerization upon intimate interaction of fibrinogen and thrombin, it is important to keep separate these two blood proteins until application to the site of use. In practice, the two components are typically dispensed simultaneously from separate syringes and brought together by means of an applicator manifold.

With the known assemblies, a generally trough- or sleeve-shaped retaining means including appropriate troughs or sleeves for receiving the syringe bodies is provided to connect the syringe bodies, which retaining means, in addition, is provided with finger grips laterally projecting in opposite directions. The syringe bodies are inserted in these retaining means, wherein for instance, elastically yielding snap-in projections hold fast the syringe bodies. To actuate the pistons of the syringe bodies, the piston rods that are firmly connected with the pistons, furthermore, are connected with a common grip element, and, for stabilizing and improving the guidance of the piston rods when actuating the syringe device, it has also been proposed to connect a guide rod with the common grip element; such guide rod extends through a guide bore within the retaining means.

By such a design, a substantial progress in terms of simple mounting and greater safety in manipulation has been achieved as compared to earlier designs, such as according to U.S. Pat. Nos. 3,223,083 or 2,112,160, since, on the one hand, the syringe bodies may, for instance, be snapped in the retaining means and, on the other hand, the piston rods are interconnected for jointly operating the pistons and, moreover, are guided by the guide rod when moved such that a uniform actuation of the pistons of all of the syringe bodies will be ensured. By contrast, with the arrangement according to U.S. Pat. No. 2,112,160, the syringe bodies, which directly contact each other longitudinally, are connected in a complex manner by a cement mass as well as by wire loops and rubber bands. With the arrangement according to U.S. Pat. No. 3,223,083, the syringe bodies are connected with one another by a clamp enclosing them on a central point, wherein the syringe bodies do not assume a stable position relative to one another. Moreover, the two piston rods must be pushed forward by the user simultaneously and as uniformly as possible, which requires great skill.

In U.S. Pat. No. 5,290,259, there is disclosed a double syringe delivery system for holding a pair of syringes in a manner so as to accommodate the simultaneous activation of the plunger of each syringe in order to effect simultaneous delivery of the contents of each syringe, each syringe containing different contents. The double syringe delivery system includes an elongated support member that is placed between the barrel of each syringe. The elongated support member has resilient, C-shaped clamps on opposite sides of the support member. The clamps are used for holding the syringe barrels of both syringes so that the syringe barrels will be held together in a parallel manner. Further, elongated support member and clamps hold the syringe barrels in a fashion that is slightly longitudinally offset from one another to permit the two syringe barrels to be held together as closely as possible. An interconnecting bridge member connects the two syringe plungers so that they can also be simultaneously activated even though they are also slightly longitudinally offset from one another.

SUMMARY OF THE INVENTION

The present invention provides a double syringe delivery system that seeks to overcome many of the problems and disadvantages experienced in the prior state of the art. The double syringe delivery system of the present invention is useful in any art in which two nonhomogeneous components must be kept separate and are delivered separately but simultaneously, wherein the individual components are combined at the delivery site. Non-limiting examples of such fields include the production of fibrin glue (e.g., by simultaneously delivering fibrinogen-containing solutions with thrombin-containing solutions from separate syringes), and the field of dentistry.

More specifically, the present invention provides a dual syringe delivery system designed so that it can be gripped comfortably and which permits simultaneous application of the two nonhomogeneous materials contained in two separated syringes. The apparatus is comprises of a pair of syringe bodies which are held in parallel relationship with respect to one another by a holding mechanism and a plunger clip. The delivery ends of the individual syringe bodies are connected to a delivery mechanism. The plunger clip allows for even, simultaneous and accurate delivery of the separate components contained in each syringe body.

A further aspect of the present invention is to provide a double syringe delivery system capable of utilizing two standard syringes of different lengths, wherein the syringe plungers are locked together with a plunger clip designed to accommodate the offset relationship of the plungers so that the syringe plungers can be simultaneously activated to expel all of the contents of the fluids contained in both syringes.

Briefly described, in one embodiment of the double syringe delivery system of the present invention, the delivery system comprises a holding mechanism having an elongated support member that is interposed between the syringe barrels of two standard syringes. The elongated support member has two resilient C-shaped clamps which are spaced from on one end of the support member. The C-shaped clamps can be snapped onto a delivery tip that is connected to the syringe barrels of each of the syringes. In this fashion, the two syringes will be held together in a parallel manner. Also attached to the support member are two finger grips to aid in the delivery of the syringe contents. The double syringe delivery system also comprises a plunger clip that attaches to the end of the syringe plungers so as to join the syringe plungers together to permit simultaneous actuation of the syringe plungers. Since the holding mechanism attaches to the delivery tip rather than the syringes, the dual syringe delivery system of this invention is independent of syringe size or length. Accordingly, any combination of syringe sizes can be attached to the delivery tip without requiring design changes to the holding mechanism.

The delivery system of this invention further comprises a syringe plunger clip. The clip attaches the two plungers together for even and accurate delivery of the two components. A key feature to this design is the offset of the two slots to compensate for the difference in length of the two syringes. The offset is set to ensure each syringe is emptied at the same time without residual fluid remaining in either syringe.

In one embodiment, the present invention relates to a delivery system for applying a tissue adhesive. More particularly, the tissue adhesive is comprised of a first solution containing fibrinogen and a second solution containing thrombin. The delivery system is used to keep these two solutions separate until they are applied together at a treatment site to seal a wound, stop bleeding or the like.

BRIEF DESCRIPTION OF THE DRAWINGS

The accompanying drawings, which are incorporated herein and form a part of the specification, illustrate preferred embodiments of the present invention, and together with the description, serve to explain the principles of the invention.

In the Drawings.

DETAILED DESCRIPTION OF THE INVENTION

Figure 1:
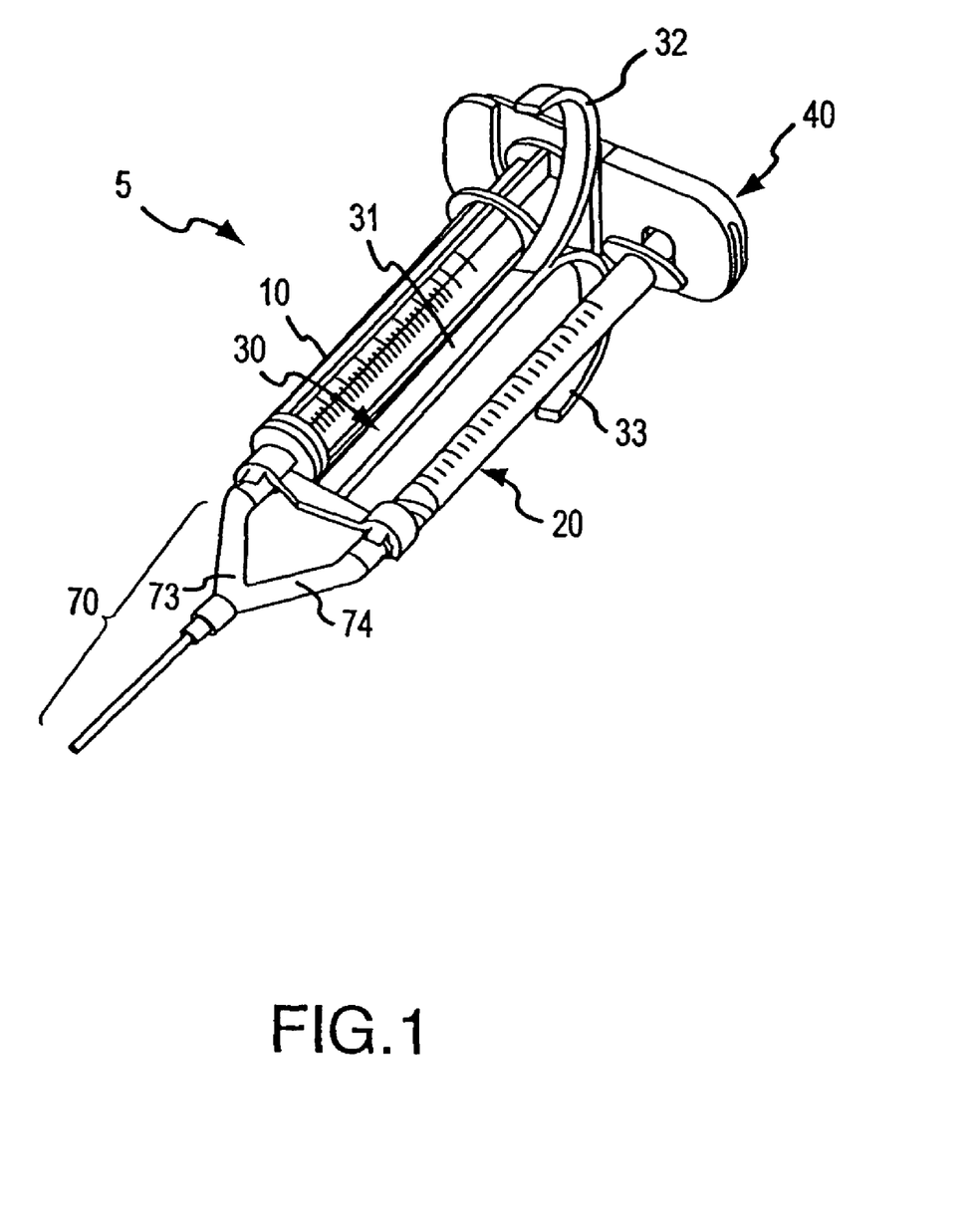
FIG. 1 is a plan view of a delivery system of this invention assembled with two syringes.
Figure 2:
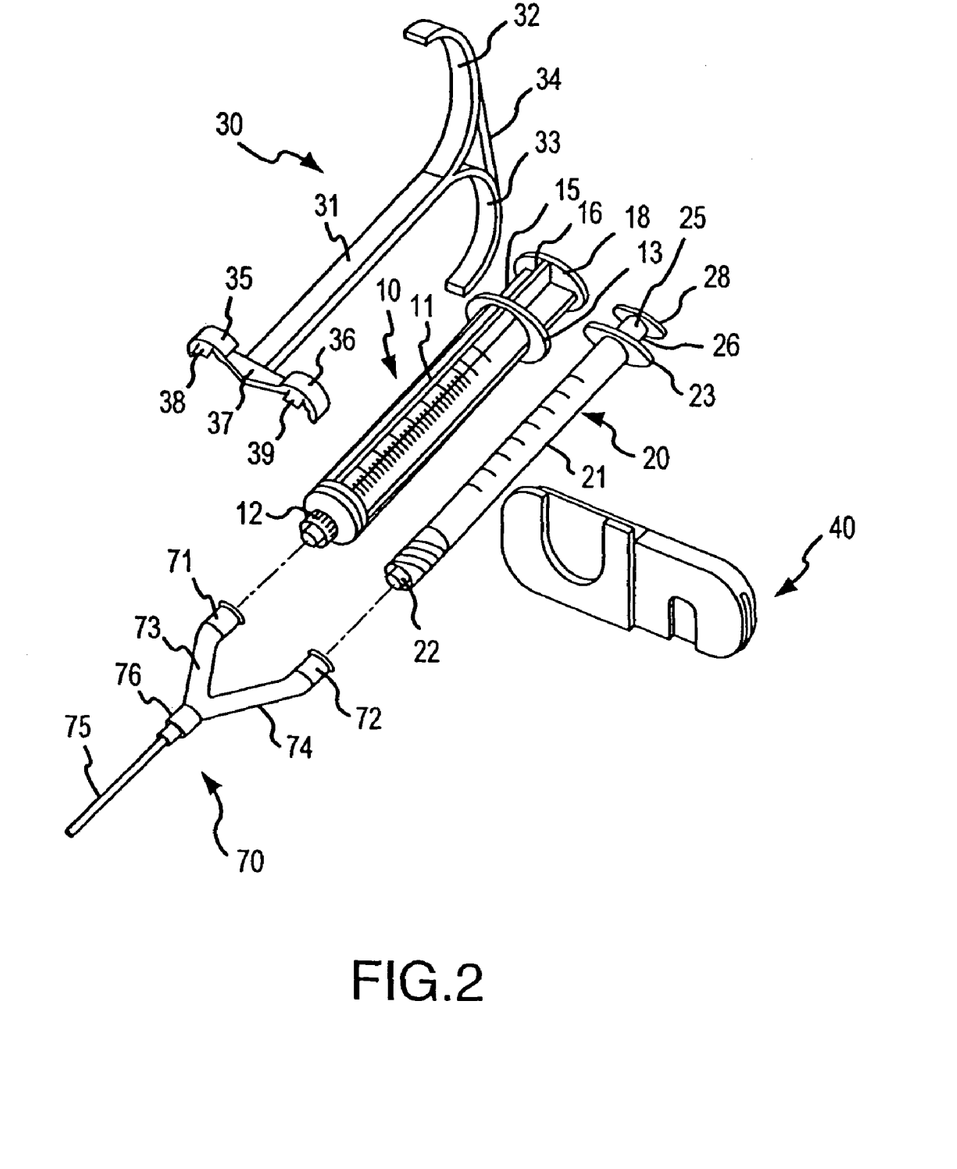
FIG. 2 is an exploded view of a delivery system of this invention showing the individual components.

FIGS. 1 and 2 illustrate one embodiment of a double syringe delivery system in accordance with present invention, as generally indicated at reference numeral 5. The double syringe delivery system is used for holding a pair of standard syringes in a manner so as to accommodate simultaneous activation of the plunger of each syringe in order to effect simultaneous delivery of the contents of each syringe barrel.

As shown in FIGS. 1 and 2, the apparatus of the present invention comprises a pair of syringes (10, 20). Each syringe (10, 20) has a syringe barrel (11, 21) from which fluid is to be dispensed. The syringes (10, 20) can either be the same size or can be different sizes and/or lengths. Associated with each syringe barrel is a syringe plunger (15, 25) which is inserted into the end of the syringe barrel (11, 21) in standard fashion so that as the syringe plunger (15, 25) is pushed into the barrel (11, 21), the fluid contents of the barrel (11, 21) are dispensed. The overall length of plunger 15 can be the same as, or different than, the overall length of plunger 25. Each of the plungers has an elongated shaft (16, 26) and a push flange (18, 28) at the proximal end of the plunger shaft. The push flanges (18, 28) are held together by plunger clip 40 so that the two plungers can be actuated simultaneously. Plunger clip 40 is designed to accommodate any size syringe plunger, and ensures that the distal ends of the plungers are aligned with each other, as will be hereinafter more fully described. Each syringe barrel (11, 21) has a standard luer connector or conus (12, 22) at the delivery end of the barrel (11, 21). In the illustrated embodiment, the luer connectors (12, 22) are standard threaded female luer connectors.

Delivery apparatus 5 further comprises delivery tip 70 comprising a pair of connectors (71, 72) such as corresponding male luer connectors for the barrel connectors (12, 22). Connectors 71, 72 are used to attach application tip 70 to the coni or luer connectors 12, 22 of the syringe barrels. Attached to each connector 71, 72 of the delivery tip is a separate cannula 73, 74, respectively, through which the fluid content of the corresponding syringe 10, 20 is expelled. The distal ends of the cannulas (73, 74) are aligned with each other so that there will be simultaneous delivery of the separated fluids from both syringes to the application site. Delivery tip connectors 71, 72 have a central lumen therethrough which is in communication with each interchamber of the syringe body and with the cannula (73, 74) associated with each connector.

In one embodiment, cannulas 73, 74 comprise needles of substantially equal length. Each of these needles 73, 74 is bent towards each other to that as the needles approach their distal ends, they run parallel to each other and touch. The parallel portions of needles 73, 74 can be joined together with a sleeve, adhesive, or other methods known in the art. In another embodiment, cannula 73, 74 comprise flexible tubing which are cut off at equivalent lengths and attached at their distal ends, usually with solvent adhesive. In yet another embodiment, delivery tip 70 comprises a hollowed double fluid path attached to a single cannula fitting 75 such as that described in U.S. Pat. No. 5,104,375, which is specifically incorporated herein by reference.

Alternatively, the barrel connectors or coni (12, 22) can be attached to a spraying head device. Spraying heads for delivering fluids from syringes are well known in the art.

Another important feature of the present invention is the removable holding mechanism 30, as shown in FIGS. 1 and 2. Holding mechanism 30 includes integrally formed lateral finger grips 32, 33 which project outwardly from the proximal end of an elongated support member 31 of holding mechanism 30. The finger grips (32, 33) provide a means by which the apparatus can be gripped comfortably by the user in any number of angular orientations. In one embodiment, a bridge member 36 is integrally formed between the finger grips (32, 33). When the delivery apparatus is assembled, support member 31 is positioned between the syringes (10, 20), and the finger grips (32, 33) project in a plane that is perpendicular to the syringes (10, 20) to reduce the width and overall profile of the dual syringe delivery system 5.

The holding mechanism 30 further comprises a collar means at the distal end of the support member 31. With reference to FIG. 2, the collar means is comprised of two resilient C-shaped clamps (35, 36) that can be removably snapped onto the connectors (71, 72) of delivery tip 70 for purposes of securely holding the syringes (10, 20) in a substantially parallel manner, and so that the delivery ends of the syringes (10, 20) are aligned with each other. In the embodiment shown in FIG. 2, C-shaped clamps 35 and 36 are formed on either end of bridge 37, which is perpendicularly formed at the distal end of support member 31. The width of each clamp (35, 36) is large enough so that each clamp can be snapped onto a connector (71, 72) of the delivery tip 70, but narrow enough to ensure a secure fit. As will be further appreciated from FIGS. 1 and 2, the entire holding mechanism 30 is preferably constructed as a unitary, molded plastic piece which has sufficient resilience or memory so that the C-shaped clamps (35, 36) can be easily snapped onto and off of the delivery tip 70, thus permitting interchangeability of the syringes (10, 20) without disassembling the entire delivery apparatus.

In one embodiment, each C-shaped clamp (35, 36) includes a knob (38, 39) integrally formed approximately midway between the ends of the clamp and projecting towards the delivery tip 70. The knobs (38, 39) serve to stabilize holding mechanism 30 during use of the delivery system 5 of this invention.

Since holding mechanism 30 of this invention is secured to the connectors (71, 72) of the delivery tip 70 rather than to the syringe barrels 11, 21, the delivery system of this invention is independent of syringe size. Accordingly, any combination of syringe sizes can be utilized in the delivery apparatus 5 of this invention without requiring design changes to holding mechanism 30.

In one embodiment of this invention, holding mechanism 30 and delivery tip 70 integral, i.e., they are formed as a unitary, molded piece.

The delivery system 5 of this invention further comprises a syringe plunger clip 40. Plunger clip 40 is removably secured to the flange (18, 28) of each syringe plunger (15, 25) and provides a surface against which the finger(s) of a user can be pushed when exerting pressure on the plungers (15, 25). Plunger clip 40 thus aids the simultaneous actuation of the plungers (15, 25) with equal stroke. Plunger clip 40 has a unique configuration which permits it to be slipped onto and off of the push flanges (18, 28) by the user without having to disassemble the entire delivery device. In addition, plunger clip 40 is able to compensate for the difference in length when syringes 10, 20 are different lengths as described hereinafter in detail. This feature ensures that each syringe is emptied at the same time without residual fluid remaining in either syringe, regardless of the size of the syringe.

Figure 3:
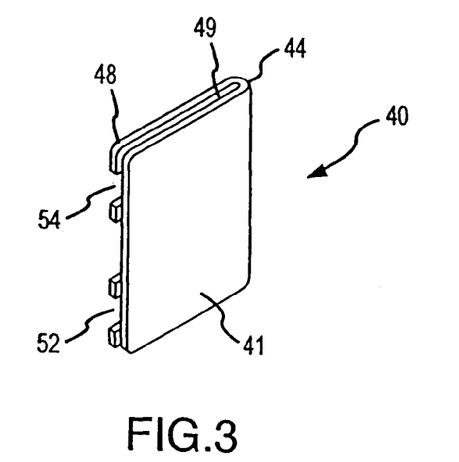
FIG. 3 is side plan view of one embodiment of a plunger clip of this invention.
Figure 4:
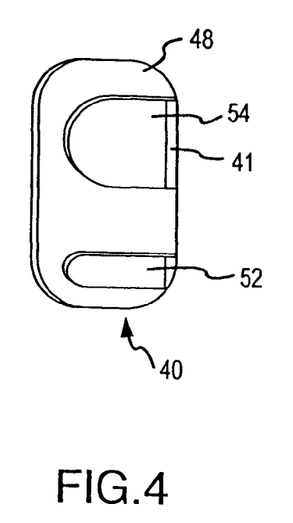
FIG. 4 is a side plan view of the plunger clip of FIG. 3.

With reference to FIGS. 3 and 4, one embodiment of plunger clip 40 comprises a solid top member 41, one or more side members 44 projecting downwardly from at least one, but less than all, of the sides of top member 41, and a base member 48 which projects from side member 44 and is substantially parallel to the top member 41, forming a gap 49 therebetween. In one embodiment, members 41, 44 and 48 are all formed as a unitary, molded plastic piece. Base member 48 also includes grooves 52 and 54 for receiving push flanges 18 and 28, respectively. In one embodiment, grooves 52, 54 are proportioned so they are larger than the diameter of plunger shafts 16 and 26, but smaller than the diameter of push flanges 18 and 28. This configuration permits the push flanges to be removably yet securely clipped within and retained by plunger grip 40 so that the two plungers (15, 25) can be actuated simultaneously. The distance between grooves 52, 54 is wide enough to allow support member 31 to be positioned between barrels 11, 21 when the device 5 is assembled. Plunger clip 40 is made of a resilient material such as a plastic having sufficient flexibility so that flanges 18, 28 can be inserted into grooves 52, 54, but has sufficient stiffness to ensure that the flanges are securely retained between top member 41 and base member 48.

In the embodiment illustrated in FIG. 4, grooves 52, 54 of plunger clip 40 have different lengths and/or widths and are sized to accommodate a pair of syringes of specific yet different sizes. For example, in one nonlimiting embodiment, groove 52 is sized to securely retain the plunger of a 5 mL syringe, and groove 54 is sized to securely retain the plunger of a 10 mL syringe. In this embodiment, groove 54 is wider than, and optionally longer than, groove 52.

Figure 6:
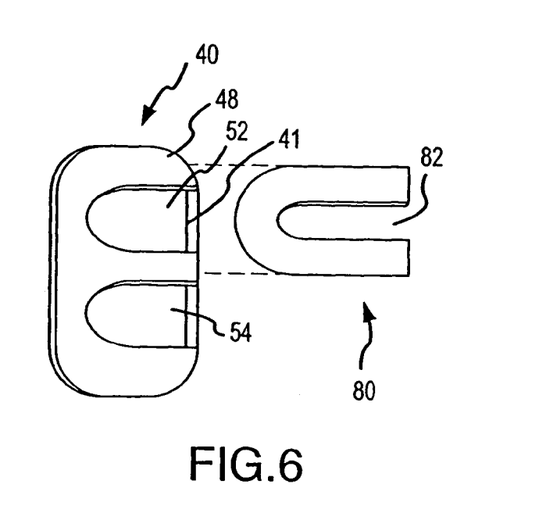
FIG. 6 is an exploded view of one embodiment of a plunger clip and an insert for one of the clip grooves.

In an alternative embodiment of plunger clip 40, grooves 52, 54 are substantially the same width. By way of illustration only, in one embodiment of plunger clip 40 the grooves 52, 54 are substantially the same width and are wide enough to securely retain a plunger of a 20 mL syringe. In this embodiment, if a smaller syringe (e.g., smaller than a 20 mL syringe) having a plunger narrower than a 20 mL syringe is required, the narrower syringe plunger can be securely retained by plunger clip 40 by one of several means. One means of retaining the narrower syringe plunger within plunger clip 40 utilizes a resilient insert 80 as illustrated in FIG. 6, which can be made of a resilient rubber or plastic material. In the embodiment illustrated in FIG. 6, flexible insert 80 has an overall width wider than the width of groove 52 and overall length longer than groove 52. Insert 80 further comprises groove 82 having a width that is narrower than the width of groove 52. In use, the insert 80 is inserted into between top member 41 and base member 48 prior to sliding the push flange of the narrower plunger into groove 52 so that grooves 52 and 82 are substantially centered. In this manner, insert 80 essentially narrows the width of the groove into which the flange of the narrower plunger is inserted, thereby creating a more secure fit for the narrower plunger. The flange of the narrower plunger is then inserted into groove 82 between top member 41 and insert 80. The insert 80 has sufficient flexibility to allow a plunger that is slightly wider than groove 82 to be inserted into groove 82, but has sufficient stiffness to ensure that the inserted flange is securely retained.

Figure 7:
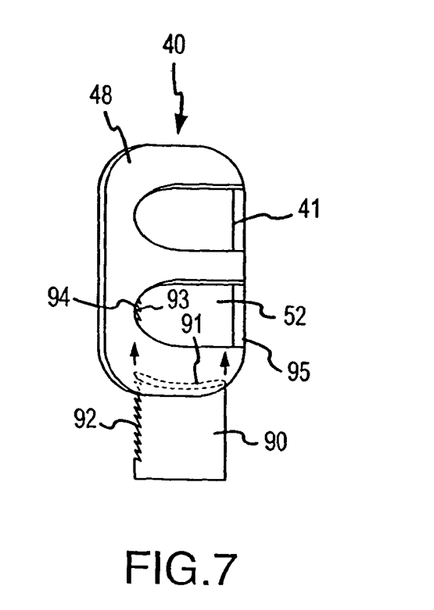
FIG. 7 is an exploded view of one embodiment of a plunger clip and an alternative insert for one of the clip grooves.

An alternative method of retaining a narrower plunger into a wider groove 52 of plunger clip 40 having grooves of substantially the same width is illustrated in FIG. 7. In this embodiment, a ratcheted insert 90 is provided to ensure a tighter fit of a narrower plunger into a wider groove 52. With reference to FIG. 7, ratcheted insert 90 comprises a curved wall 91 for pressing against the plunger. Insert 90 further comprises ratchet teeth 92 extending longitudinally from a second wall adjacent to the curved wall 91 and having preselected transverse spacings therebetween. In this embodiment, groove 52 of plunger clip 40 further comprises ratchet teeth 93 extending longitudinally from the concave side 94 of groove 52. Ratcheted insert 90 may be inserted into groove 52 in such a manner that ratchet teeth 92 on insert 90 slidingly engage ratchet teeth 93 on the concave side 94 of groove 52. Ratchet teeth 92, 93 may be formed such that each rib includes a vertical and a slanted side when viewed in cross section. Ratchet teeth 92, 93 are ideally constructed such that they slidingly mesh when insert 90 is inserted into gap 52 between top member 41 and base member 48. Because of the relative orientations of the vertical and slanted sides of ratchet teeth 92 and 93, insert 90 may be irreversibly inserted into gap 52. Ratchet teeth 92, 93 thus behave like the pawls of a ratchet, permitting movement in one direction past them, but prohibiting movement past them in the opposite direction. In use, the flange of the narrower plunger is first inserted into groove 92. Insert 90 is then inserted into gap 49 from a side adjacent opening 95 of groove 52 until curved wall 91 abuts the narrower plunger shaft. In this manners the narrower plunger is securely retained by the plunger clip 40.

Figure 5:
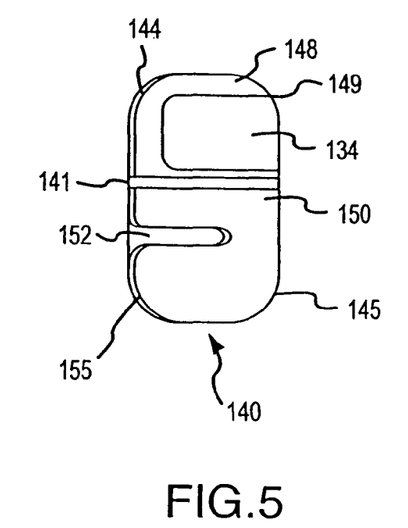
FIG. 5 is a side plan view of an alternative plunger clip of this invention.

An alternate embodiment of a delivery apparatus of this invention utilizes plunger clip 140 as illustrated in FIG. 5. Plunger clip 140 comprises a top member 141, a first side member 144 projecting downwardly from top member 141, and a first base member 148 projecting inwardly from side member 144 and parallel to top member 141, forming a gap 149 therebetween. Plunger clip further comprises second side member 145 projecting downwardly from top member 141 from a side opposite that of first side member 144, and a second base member 150 projecting inwardly from side member 145 and parallel to top member 141, forming a gap 155 therebetween. Base members 148 and 150 also include grooves 152 and 154, respectively, for receiving push flanges 18, 28. Grooves 152, 154 of plunger clip 140 open from opposite sides of plunger clip 141. An advantage of this design is that the plunger clip 140 can be rotated about one of the plungers out of the way of the second plunger, making it easier to replace the second syringe without disassembling the entire delivery device. In one embodiment of plunger clip 140, grooves 152 and 154 of plunger clip 140 have different lengths and/or widths, and plunger clip 140 is thus designed to accommodate a pair of syringes of specific yet different sizes. In an alternative embodiment of plunger clip 140, grooves 152, 154 are substantially the same width, and a narrower syringe plunger can be securely retained by plunger clip 140 by one of several means, such as by utilizing insert 80 (FIG. 6) or ratcheted insert 90 (FIG. 7) as described above.

With reference to FIG. 1, in one method of using the double syringe delivery system of the present invention, two standard syringes 10, 20 are first obtained and the delivery tips 70 is attached at the delivery ends of each syringe barrel 11, 21 in the manner described. Each connector 71, 72 of delivery tip 70 is snapped into the two resilient, C-shaped clamps 38 and 39 of holding mechanism 30 to secure the two syringes 10, 20 in a parallel relationship. The plunger clip 40 is secured to the proximal ends of each syringe plunger 15, 25 by sliding the flange 18, 28 of each syringe plunger 15, 25 into grooves 52, 54. Syringe plungers 15, 25 can be simultaneously activated by gripping the finger grips 32, 33 with two fingers and pushing against the plunger clip 40, for example, with the palm or heal of the hand, in order to simultaneously express, either drop-wise or faster, the fluid contents of each syringe 10, 20 which are thereafter mixed at the site of application. By commonly depressing the respective plungers of the two syringes 10, 20, the contents of the separate syringes are expressed, dispensed or exhausted separately but simultaneously through their corresponding separate cannulas 73, 74. As they are expressed, the two separate fluid components merge at the distal terminus of the delivery tip 70. Thus, when the equivalent amounts of pressure are provided, the delivery tip 70 is able to deliver the same amount of fluid from each syringe 10 and 20.

In one embodiment, syringes of different lengths may be utilized in the delivery apparatus of this invention. Since the delivery tip 70 always ensures that the delivery ends of the syringes are substantially aligned, an alternative plunger clip designed to ensure that the contents of both syringes are emptied at the same time must be used. Accordingly, in this embodiment, the grooves of the plunger clip are offset to accommodate syringes of differing lengths.

Figure 8:
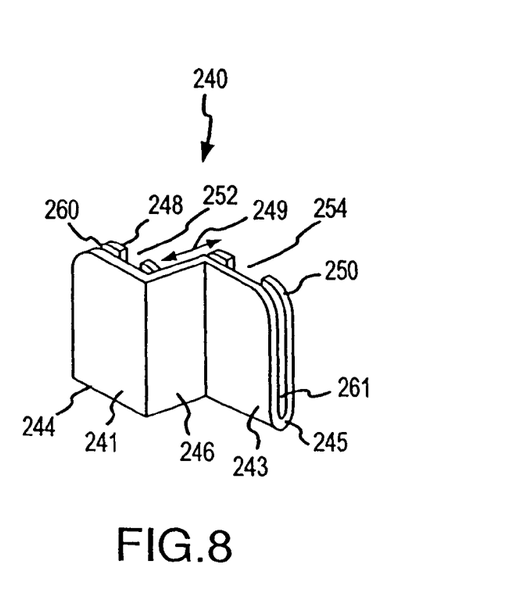
FIG. 8 a perspective view of an offset plunger clip of this invention.

One non-limiting example of an offset plunger clip 240 is illustrated in FIG. 8. Plunger clip 240 is designed so that the grooves of the plunger clip are longitudinally offset by an amount that is substantially the same as the difference in the lengths of the two syringes. With continued reference to FIG. 8, plunger clip 240 comprises first top member 241, first side member 246 projecting downward from one edge of top member 241 and a second side member 244 projecting downward from an adjacent edge of top member 241. Plunger clip 240 further comprises a second top member 243 extending outward from an edge of side member 246 opposite from top member 241 and projecting in a direction opposite that of top member 241. A third side member 245 projects downward from another side of second top member 243. Projecting inward from side members 244 and 245 are base members 248 and 250, respectively, forming gaps 260, 261, respectively, therebetween. The distance 249 between the top face of top member 241 and the top face of top member 243 is substantially equal to the difference in length between two different size syringes barrels 11, 21. Base members 248 and 250 also include grooves 252, 254, respectively.

In one embodiment of plunger clip 240 illustrated in FIG. 8, grooves 252 and 254 of plunger clip 240 have different lengths and/or widths, and plunger clip 240 is thus designed to accommodate a pair of syringes of specific yet different sizes. In an alternative embodiment of plunger clip 240, grooves 252, 254 are substantially the same width, and a narrower syringe plunger can be securely retained by plunger clip 240 by one of several means, such as by utilizing insert 80 (FIG. 6) or ratcheted insert 90 (FIG. 7) as described above. In yet another embodiment of plunger clip 240, the openings of grooves 252 and 254 into which the plungers are inserted open in opposite sides of the clip.

Figure 9:
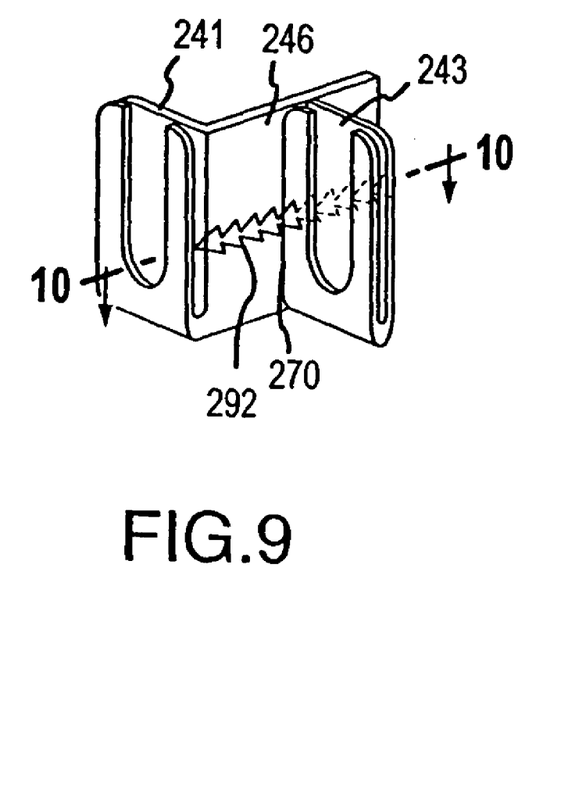
FIG. 9 is a perspective view of an offset plunger clip of this invention, showing a ratchet system.
Figure 10:
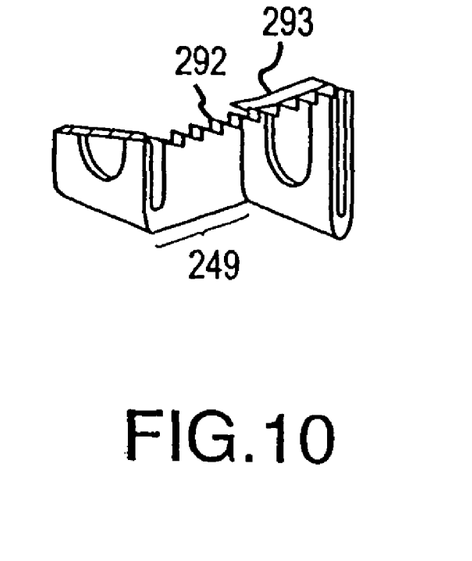
FIG. 10 is a perspective view of an adjustable offset plunger clip of this invention shown in FIG. 9 cut away along lines 10 of FIG. 9.

In one embodiment of plunger clip 240, the distance 249 between top members 241 and 243 is fixed. Alternatively, the distance 249 is made variable by employing a ratchet system in a variable plunger clip as illustrated in FIG. 9. As shown in FIG. 9, a unidirectional ratchet system is provided by ratchet teeth 292 extending longitudinally from side member 246 with a preselected transverse spacing therebetween, and tooth 293 extending longitudinally from an edge 270 of top member 243 adjacent side member 246 (see FIG. 10). Ratchet teeth 292 and tooth 293 may be formed such that each tooth includes a vertical and a slanted side when viewed in cross section. Ratchet teeth 292 and tooth 293 are ideally constructed such that they slidingly engage when top member 243 is pushed in the direction of top member 241. Because of the relative orientations of the vertical and slanted sides of ratchet teeth 292 and tooth 293, top member 243 may be moved unidirectionally towards top member 241, thereby adjusting (i.e., decreasing) distance 249 therebetween. When in use, plunger flanges 18 and 28 having different lengths are inserted into grooves 252 and 254, respectively. Base member 243 is then pushed towards base member 241 until the distal ends of plungers 15 and 25 are aligned with each other. Because of the relative orientations of the vertical and slanted sides of ratchet teeth 292 and tooth 293, base member 243 cannot be pulled back away from base member 241. The plungers 15, 25 are inserted into barrels 11, 21 and fluid is taken up into barrels 11, 21 by pulling on plunger clip 240, thereby actuating plungers 15, 25 simultaneously. To simultaneously express the fluids contained in barrels 11, 21, the user pushes against top member 241 of plunger clip 240 in order to avoid changing the adjusted distance 249.

One embodiment of the present invention is directed toward a delivery device for the production of autologous thrombin and autologous platelet gels. For example, one embodiment the present invention relates to a two-phase method for forming an autologous bioadhesive sealant composition or fibrin glue, wherein all of the blood components for the bioadhesive sealant are derived from a patient to whom the bioadhesive sealant will be applied. This method is similar to that disclosed in U.S. patent application Ser. Nos. 09/063,338 and 10/116,729, each of which is assigned to the assignee of the present invention and is specifically incorporated herein by reference. Briefly, in one embodiment a platelet rich plasma is formed by centrifuging a quantity of anticoagulated whole blood that was previously drawn from the patient. The platelet rich plasma is then divided into two portions. To the first portion, which is used in phase-one, a compound that reverses the effect of the anticoagulant is added, and a clot is allowed to form. The clot is then triturated to produce a serum containing autologous thrombin. The serum obtained from phase-one is then mixed with the second portion of the platelet rich plasma in phase-two to form a bioadhesive sealant.

Figure 11:
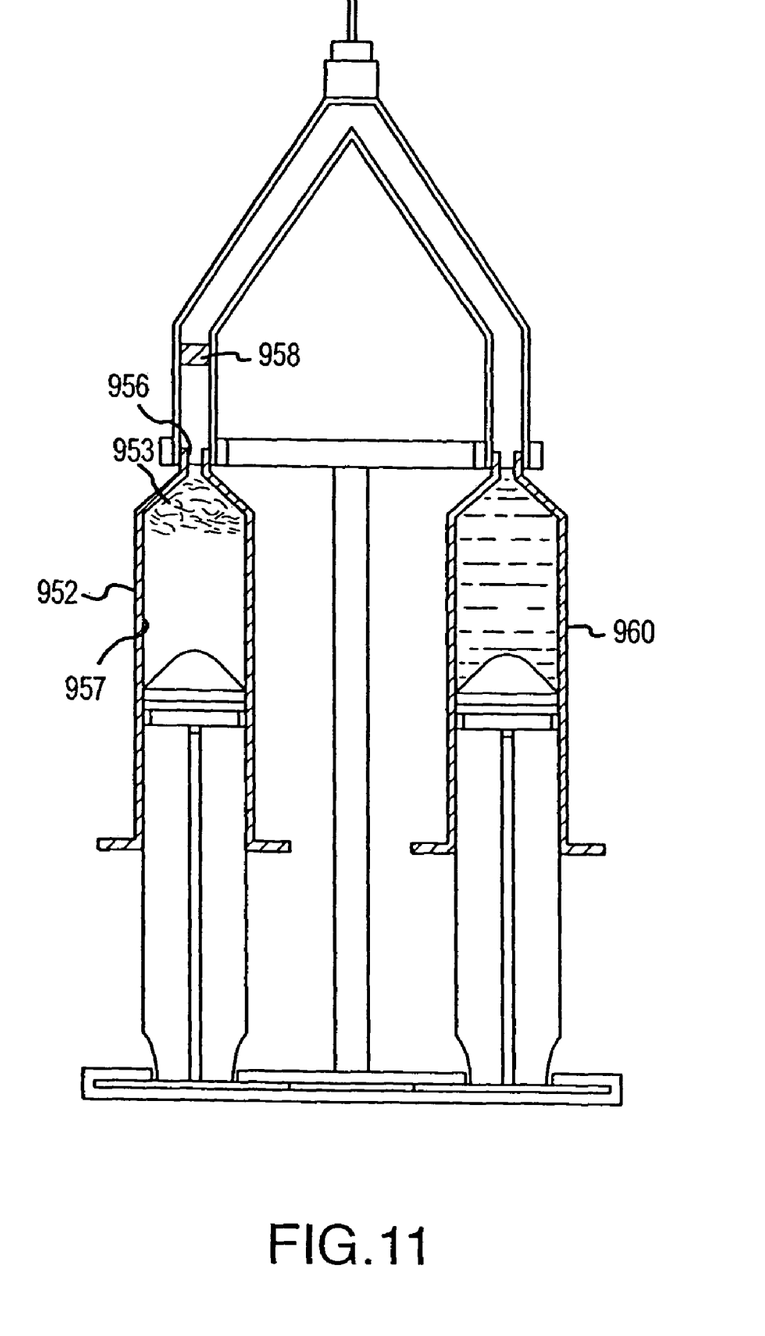
FIG. 11 is a cross-sectional view of one embodiment of a delivery system of this invention for the delivery of an autologous fibrin sealant.

More specifically, and with reference to FIG. 11 the two-phase method of forming an autologous platelet gel begins by forming anticoagulated whole blood, which is achieved by collecting a patient's whole blood in a medium containing an anticoagulation agent, such as sodium citrate (citrate) or heparin. The anticoagulated whole blood is next centrifuged at a rate of approximately 20-50 r.c.f.'s (relative centrifugal force) for 10-40 minutes, and preferably in a refrigerated centrifuge at 25 r.c.f.'s for 20 minutes, resulting in the formation of two liquid phases. The top phase is a platelet rich plasma, and the bottom phase is anticoagulated whole blood minus the platelet rich plasma. In one embodiment, the platelet rich plasma is then gently drawn off, divided into two portions and stored in syringes 952 and 960. The platelet rich plasma in syringe 952 is used in the first phase of the process to prepare the thrombin, while the second portion in syringe 960 is utilized in phase two. Syringes 952 and 960 may be either glass or plastic syringes. Preferably, syringe 960 is a plastic syringe.

Syringe 952 preferably contains a contact activator 953 such as, but not limited to, glass wool, silica, aluminum, diatomaceous earth, kaolin, etc. When syringe 952 is a glass syringe, the inner surface 957 of the syringe 952 acts as the contact activator. Chemical activators, such as kaolin, can also be used to speed up the clotting time; however, their subsequent removal would also be necessary.

Phase one according to one embodiment begins by restoring the clot-forming process. To accomplish this, an agent (restoration agent) capable of reversing the effects of the anticoagulation agent is added back into the first portion of the platelet rich plasma in syringe 952. If sodium citrate was used as the anticoagulant, the reversal of the anticoagulant is preferably accomplished using calcium chloride. However, any substance that is known or found to be functionally equivalent to calcium chloride, such as, calcium gluconate, in restoring the coagulation activity of citrated blood may be used in the practice of the present invention. Alternatively, if heparin was used as the anticoagulant, then heparinase or any other suitable anticoagulant reversing compound would be used to reverse the effect of the anticoagulation agent. The concentration of the restoration agent used to reverse the anticoagulation will depend in part, upon the concentration of the anticoagulation agent in the platelet rich plasma and the stoichiometry of the chelating and coagulation reactions. However, the concentration of the restoration agent used to reverse the anticoagulation must be sufficient to achieve clot formation.

Upon restoration of the platelet rich plasma, a clot will naturally form. The resulting clot is then triturated. In one embodiment, the clot is triturated by squeezing the clot through material 953, which in one embodiment is glass wool and thus serves not only as a contact activator but also as a filter, thus expressing thrombin. Alternatively, or in addition, a filter-958 having a large micron pore size is positioned downstream of outlet 956 of syringe 952, thereby allowing the removal of clot debris and any activator or solids that are present. The thrombin produced in syringe 952 and the second portion of platelet rich plasma (PRP) contained within syringe 960 are then expelled through their respective cannulas 73 and 74, whereupon they combine at the site of application to form the platelet gel composition.

The foregoing description is considered as illustrative only of the principles of the invention. Further, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:

1. A method of delivering a composition to a patient comprising:

centrifuging anticoagulated blood to obtain a platelet rich plasma;

placing a first portion of the platelet rich plasma in a first syringe body;

adding to the first syringe body an agent for reversing the effects of an anticoagulant within the first portion of the platelet rich plasma and allowing a clot to form within the first syringe body;

placing a second portion of platelet rich plasma in a second syringe body;

delivering thrombin from the first syringe body to the patient by squeezing the clot contained in the first syringe body through a filter material; and delivering simultaneously the second portion of the platelet rich plasma from the second syringe body to the patient to combine with the thrombin delivered to the patient from the first syringe body to form a platelet gel composition.

2. The method of claim 1 wherein the first and second syringe bodies have a luer connector at one end.

3. The method of claim 2 wherein an applicator tip comprising first and second luer fittings is connected to the luer connectors of the first and second syringe bodies.

4. The method of claim 3 further comprising the step of placing the first and second syringe bodies in a holding mechanism that retains the syringe bodies in parallel alignment without contacting said first and second syringe bodies, the holding mechanism comprising an elongated support member positioned between the first and second syringe bodies and having a pair of C-shaped clamps extending laterally from one end of the elongated support member for attachment to the applicator tip luer fittings.

5. The method of claim 1 wherein the first and second syringe bodies have first and second plungers, respectively, for delivering from each of the syringe bodies its associated material, the first and second plungers each having a push flange and a plunger shaft.

6. The method of claim 5 further comprising the step of placing the push flanges of the first and second plungers in a plunger clip having first and second channeled grooves for securing the plunger push flanges within the first and second grooves and actuating the plungers simultaneously.

7. The method of claim 6 wherein the first syringe body has a first length and the second syringe body has a second length, the first syringe body length being a different length than the second syringe body length and the first and second grooves of the plunger clip are longitudinally offset by an amount that is substantially the same as the difference in the lengths of the first and second syringe bodies.

8. The method of claim 1 wherein the platelet gel composition forms within a wound site of the patient.

9. The method of claim 1 wherein the anticoagulant is sodium citrate.

10. The method of claim 1 wherein the anticoagulant is heparin.

11. The method of claim 1 wherein the anticoagulated blood is centrifuged at a rate of about approximately 20 to 50 r.c.f.'s.

12. The method of claim 1 wherein the anticoagulated blood is centrifuged for about approximately 10 to 40 minutes.

13. The method of claim 1 wherein the anticoagulated blood is centrifuged refrigerated at about 25 r.c.f.'s for about 20 minutes.

14. The method of claim 1 wherein the first syringe includes a contact activator to speed up the formation of the clot.

15. The method of claim 14 wherein the contact activator is selected from the group consisting of glass, glass wool, silica, aluminum, diatomaceous earth and kaolin.

16. The method of claim 1 wherein the agent for reversing the effects of the anticoagulant is selected from the group consisting of sodium chloride, calcium gluconate and heparinase.

17. The method of claim 1 wherein the filter material is glass wool.

* * * * *